(12) United States Patent
Cheng et al.

(10) Patent No.: US 12,343,231 B2
(45) Date of Patent: Jul. 1, 2025

(54) DEVICE AND METHOD FOR DISTINGUISHING DENTAL PLAQUE FROM DENTAL CALCULUS

(71) Applicant: Quanta Computer Inc., Taoyuan (TW)

(72) Inventors: Kai-Ju Cheng, Taoyuan (TW);
Yu-Hsun Chen, Taoyuan (TW);
Hao-Ping Lee, Taoyuan (TW);
Tong-Ming Hsu, Taoyuan (TW);
Chin-Yuan Ting, Taoyuan (TW);
Shao-Ang Chen, Taoyuan (TW);
Kuan-Chung Chen, Taoyuan (TW);
Hsin-Lun Hsieh, Taoyuan (TW)

(73) Assignee: QUANTA COMPUTER INC., Taoyuan (TW)

( * ) Notice: Subject to any disclaimer, the term of this patent is extended or adjusted under 35 U.S.C. 154(b) by 324 days.

(21) Appl. No.: 17/817,409

(22) Filed: Aug. 4, 2022

(65) Prior Publication Data

US 2023/0301751 A1   Sep. 28, 2023

(30) Foreign Application Priority Data

Mar. 24, 2022  (TW) .................................. 111111081

(51) Int. Cl.
*A61C 7/00*   (2006.01)
*A61C 19/04*  (2006.01)

(52) U.S. Cl.
CPC .............. *A61C 7/002* (2013.01); *A61C 19/04* (2013.01)

(58) Field of Classification Search
CPC .................................. A61C 7/002; A61C 19/04
See application file for complete search history.

(56) References Cited

U.S. PATENT DOCUMENTS 11,471,034 B2    10/2022  Cheng et al.
2013/0034826 A1 *  2/2013  Walsh ................... A61B 1/0607
                                                              433/29

(Continued)

FOREIGN PATENT DOCUMENTS

CN       111025959 A        4/2020
EP         2554107 A1 *     2/2013    ......... A61B 1/00186

(Continued)

OTHER PUBLICATIONS

Extended European Search Report dated Aug. 18, 2023, issued in application No. EP 22191912.9.

(Continued)

*Primary Examiner* — Nicholas D Lucchesi
(74) *Attorney, Agent, or Firm* — McClure, Qualey & Rodack, LLP

(57) ABSTRACT

A distinguishing device for dental plaque and dental calculus includes a light-emitting diode, an image sensing unit, and a processor. The light-emitting diode movies in a first direction and is separated from teeth in an oral cavity by a predetermined distance in a second direction. The second direction is perpendicular to the first direction. The light-emitting diode generates a blue light to illuminate the teeth, so that dental plaque on the teeth generates a first autofluorescence and dental calculus on the teeth generates a second autofluorescence. The image sensing unit is configured to sense the first autofluorescence and the second autofluorescence. The processor is coupled to the image sensing unit to distinguish a dental plaque area from a dental calculus area on the teeth according to the first autofluorescence and the second autofluorescence.

11 Claims, 6 Drawing Sheets

(56) References Cited

U.S. PATENT DOCUMENTS

| | | | | |
|---|---|---|---|---|
| 2013/0323674 A1* | 12/2013 | Hakomori | ............... | A61B 1/043 |
| | | | | 433/29 |
| 2013/0323685 A1* | 12/2013 | Ostler | ..................... | A61K 6/79 |
| | | | | 522/64 |
| 2016/0166137 A1* | 6/2016 | Hakomori | ............... | A61C 1/088 |
| | | | | 433/29 |
| 2017/0303791 A1* | 10/2017 | Vermeulen | ......... | A46B 15/0036 |
| 2019/0231492 A1* | 8/2019 | Sabina | ................. | A61B 1/0646 |
| 2022/0274610 A1 | 9/2022 | Chen | | |

FOREIGN PATENT DOCUMENTS

| | | | |
|---|---|---|---|
| TW | 202109009 A | 3/2021 | |
| WO | WO-2016051300 A1 * | 4/2016 | ............. A46B 13/02 |
| WO | 2017/094004 A1 | 6/2017 | |

OTHER PUBLICATIONS

Qu, J.Y., et al.; "Correction of geometrical effects of fluorescence imaging of tissue;" Optics Communications; Apr. 2000; pp. 319-326.

Chinese language office action dated Jan. 30, 2023, issued in application No. TW 111111081.

Chinese language office action dated Sep. 20, 2023, issued in application No. CN 202110083175.3.

* cited by examiner

DEVICE AND METHOD FOR DISTINGUISHING DENTAL PLAQUE FROM DENTAL CALCULUS

CROSS REFERENCE TO RELATED APPLICATIONS

This application claims priority of Taiwan Patent Application No. 111111081, filed on Mar. 24, 2022, the entirety of which is incorporated by reference herein.

BACKGROUND OF THE INVENTION

Field of the Invention

The present invention relates to a distinguishing device for dental plaque and dental calculus, and, in particular, to a distinguishing device for dental plaque and dental calculus using the autofluorescence difference of dental plaque and dental calculus to distinguish dental plaque from dental calculus.

Description of the Related Art

Bacteria may cause many adverse effects on teeth, such as dental calculus, dental plaque, gingivitis, periodontal disease, and tooth decay. It is important to have regular dental examinations to detect whether teeth have dental plaque and dental calculus. However, dental plaque and dental calculus are not easily detected with the naked eye. Therefore, various dental plaque and dental calculus detection methods have been used to help detect dental plaque and dental calculus on teeth.

For example, a disclosing agent is traditionally used to distinguish dental plaque from dental calculus, but the process is trivial and it takes time to clean the stained part after detection. Therefore, being able to conveniently and quickly detect and distinguish dental plaque areas from dental calculus areas on teeth has become a challenging topic today.

BRIEF SUMMARY OF THE INVENTION

The present disclosure provides a distinguishing device for dental plaque and dental calculus. The distinguishing device includes a light-emitting diode, an image sensing unit, and a processor. The light-emitting diode moves in a first direction and separated from teeth in an oral cavity by a predetermined distance in a second direction. The second direction is perpendicular to the first direction. The light-emitting diode generates a blue light to illuminate the teeth, so that a dental plaque on the teeth generates a first autofluorescence and a dental calculus on the teeth generates a second autofluorescence. The image sensing unit is configured to sense the first autofluorescence and the second autofluorescence. The processor is coupled to the image sensing unit to distinguish a dental plaque area from a dental calculus area on the teeth according to the first autofluorescence and the second autofluorescence.

The present disclosure provides a method for distinguishing dental plaque and dental calculus. The method includes generating a blue light by a light-emitting diode to illuminate teeth in an oral cavity, so that dental plaque on the teeth generates a first autofluorescence and dental calculus on the teeth generates a second autofluorescence. The the light-emitting diode moves in a first direction and is separated from the teeth by a predetermined distance in a second direction perpendicular to the first direction. The method further includes sensing the first autofluorescence and the second autofluorescence by an image sensing unit; and distinguishing a dental plaque area from a dental calculus area on the teeth by a processor according to the first autofluorescence and the second autofluorescence.

BRIEF DESCRIPTION OF THE DRAWINGS

In order to describe the manner in which the above-recited and other advantages and features of the disclosure can be obtained, a more particular description of the principles briefly described above will be rendered by reference to specific examples thereof which are illustrated in the appended drawings. Understanding that these drawings depict only exemplary aspects of the disclosure and are not therefore to be considered to be limiting of its scope, the principles herein are described and explained with additional specificity and detail through the use of the accompanying drawings.

DETAILED DESCRIPTION OF THE INVENTION

Figure 1:
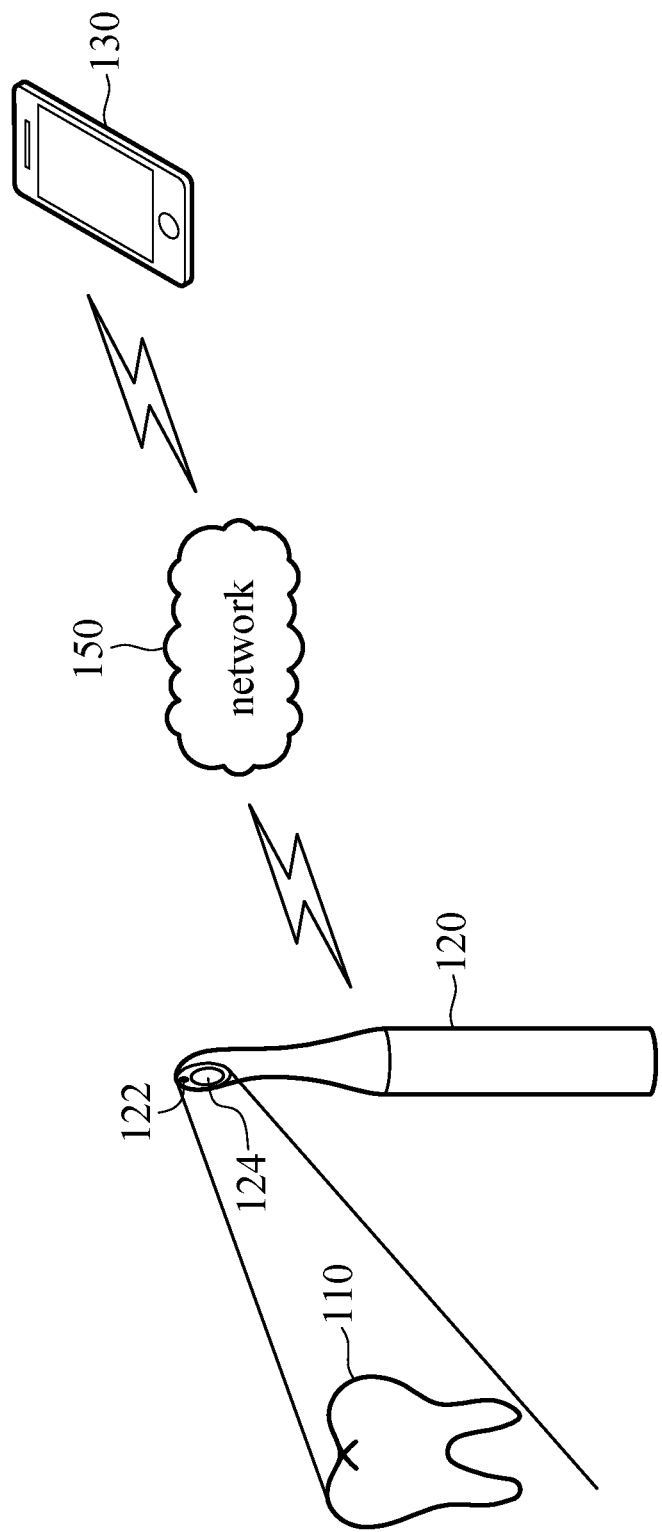
FIG. 1 illustrates a schematic diagram of a device for detecting teeth, in accordance with one embodiment of the present disclosure.

The following disclosure provides many different embodiments, or examples, for implementing different features of the invention. Specific examples of components and arrangements are described below to simplify the present disclosure. These are, of course, merely examples and are not intended to be limiting. For example, the formation of a first feature over or on a second feature in the description that follows may include embodiments in which the first and second features are formed in direct contact, and may also include embodiments in which additional features may be formed between the first and second features, such that the first and second features may not be in direct contact. In addition, the present disclosure may repeat reference numerals and/or letters in the various examples. This repetition is for the purpose of simplicity and clarity and does not in itself dictate a relationship between the various embodiments and/or configurations discussed.

For purposes of the present detailed description, unless specifically disclaimed, the singular includes the plural and vice versa; and the word "including" means "including without limitation." Moreover, words of approximation, such as "about," "almost," "substantially," "approximately," and the like, can be used herein to mean "at, near, or nearly at," or "within 3-5% of," or "within acceptable manufacturing tolerances," or any logical combination thereof, for example.

Furthermore, spatially relative terms, such as "beneath," "below," "lower," "above," "upper" and the like, may be used herein for ease of description to describe one element or feature's relationship to another element(s) or feature(s) as illustrated in the figures. The spatially relative terms are intended to encompass different orientations of the device in use or operation in addition to the orientation depicted in the figures. For example, if the device in the figures is turned over, elements described as being "below" or "beneath" other elements or features would then be oriented "above" the other elements or features. Thus, the exemplary term "below" can encompass both an orientation of above and below. The apparatus may be otherwise oriented (rotated 90 degrees or at other orientations) and the spatially relative descriptors used herein may likewise be interpreted accordingly.

The terminology used herein is for the purpose of describing particular embodiments only, and is not intended to be limiting of the invention. As used herein, the singular forms "a", "an" and "the" are intended to include the plural forms as well, unless the context clearly indicates otherwise. Furthermore, to the extent that the terms "including," "includes," "having," "has," "with," or variants thereof, are used in either the detailed description and/or the claims, such terms are intended to be inclusive in a manner similar to the term "comprising."

Unless otherwise defined, all terms (including technical and scientific terms) used herein have the same meaning as commonly understood by one of ordinary skill in the art. Furthermore terms, such as those defined in commonly used dictionaries, should be interpreted as having a meaning that is consistent with their meaning in the context of the relevant art, and will not be interpreted in an idealized or overly formal sense unless expressly so defined herein.

FIG. 1 illustrates a schematic diagram of a device 120 for detecting teeth 110, in accordance with one embodiment of the present disclosure. As shown in FIG. 1, the device 120 may at least include a light emitting diode 122, an image-sensing unit 124, and a processor (not shown in FIG. 1) that may be integrated into the device 120.

In some embodiments, the light emitting diode 122 of the device 120 may generate low wavelength light. For example, the light emitting diode 122 may generate a blue light with a wavelength in a range from 370 nm to 430 nm to illuminate the teeth 110 in the oral cavity. In some embodiments, the light emitting diode 122 may be referred to as light source. More specifically, when the light emitting diode 122 is used to generate the blue light with a low wavelength to illuminate the teeth 110 in the oral cavity, the dental plaque and the dental calculus on the teeth 110 will undergo a fluorescence reaction to generate an autofluorescence. In the present disclosure, the blue light emitted by the light emitting diode 122 has a fixed luminous intensity, and the light emitting diode 122 is movable, so that the light emitting diode 122 may illuminate the teeth 110 at different positions to affect the illuminance of the blue light received by the teeth 110.

The image sensing unit 124 may sense or capture the autofluorescence generated by the dental plaque and the dental calculus. In some embodiments, the image sensing unit 124 may be a single-point photodetector or a photosensitive element which is array type, such as a charge coupled device (CCD) or a complementary metal-oxide semiconductor (CMOS). The single-point photodetector may directly analyze a single pixel, while the photosensitive element which is array type may analyze pixels that belong to the same area of each frame by image processing methods. In the present disclosure, the image sensing unit 124 is movable, overlaps the light emitting diode 122 in a top view, and moves simultaneously with the light emitting diode 122. In other embodiments, the image sensing unit 124 does not move.

The processor may be coupled to the image sensing unit 124 to receive autofluorescences from the dental plaque and the dental calculus sensed by the image sensing unit 124, and to distinguish dental plaque areas from dental calculus areas located on the teeth 110 according to the autofluorescences.

The device 120 may be connected to an electronic device 130 through a network 150, so as to transmit an oral image including the dental plaque areas and the dental calculus areas determined by the processor to the electronic device 130. Exemplary electronic devices may include a desktop computer, a notebook, a smartphone, a personal digital assistant (PDA), a tablet, or any other device having a display screen. The user may observe the dental plaque areas and the dental calculus areas on the teeth 110 in the oral image through a display device on the electronic device 130.

The network 150 may provide wired and/or wireless networks. The network 150 may also include a local area network (LAN) (e.g., an intranet), a wireless local area network (WLAN) or a Wi-Fi network, a third generation (3G) or a fourth generation (4G) mobile telecommunications network, a wide area network (WAN), the Internet, Bluetooth, or any suitable combination thereof.

In the present embodiment, the light emitting diode 122 is integrated into the device 120. It should be understood that in other embodiments, the light emitting diode 122 may be separate from the device 120. Specifically, the device 120 may have no light emitting diodes 122, and an external light source may be used to illuminate the teeth 110 in the oral cavity. It should be noted that the device 120 may be a general electronic device, such as a dental camera or the like. Although the device 120 in FIG. 1 is shown in the form of a dental camera, it should be understood by those skilled in the art that the present disclosure is not limited thereto.

Figure 2:
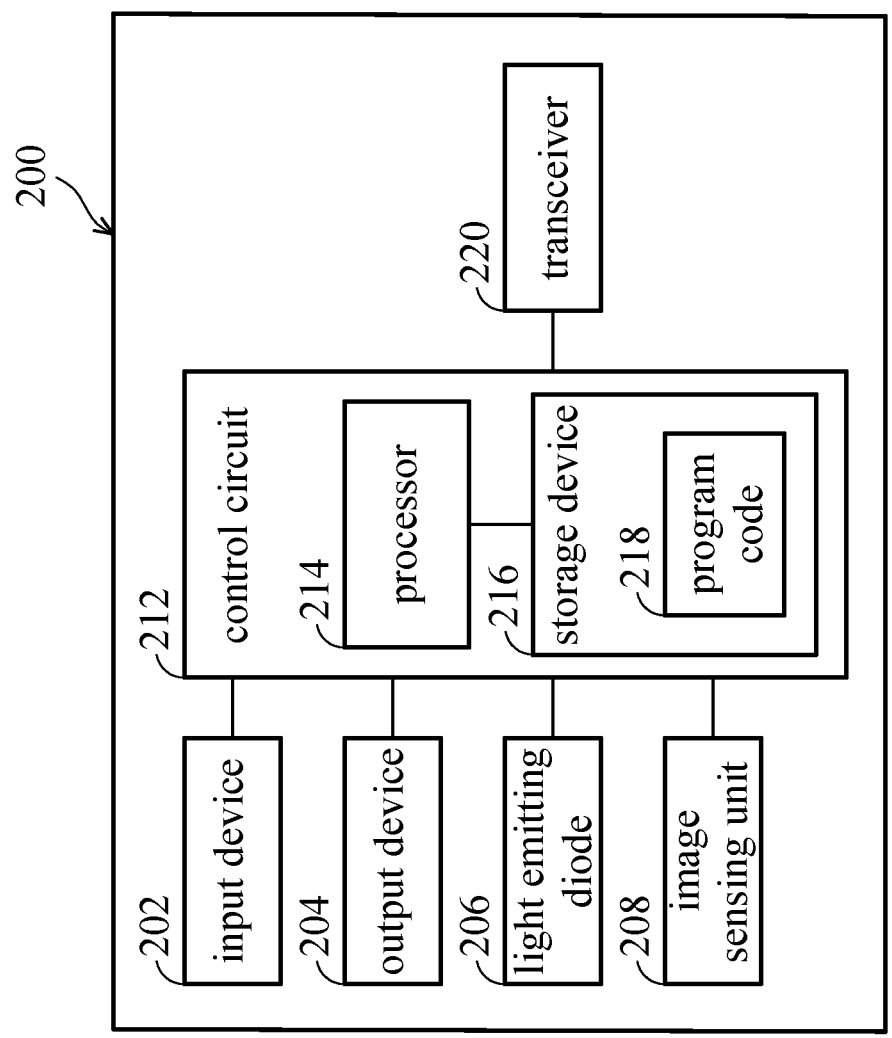
FIG. 2 illustrates a schematic diagram of a device, in accordance with one embodiment of the present disclosure.

FIG. 2 illustrates a schematic diagram of a device 200, in accordance with one embodiment of the present disclosure. As shown in FIG. 2, the device 200 may be the same as or similar to the device 120 shown in FIG. 1.

In FIG. 2, the device 200 may include an input device 202, an output device 204, a light emitting diode 206, an image sensing unit 208, a control circuit 212, and a transceiver 220. The control circuit 212 may include a processor 214 and a storage device 216. It should be understood that other configurations and inclusion or omission of various items in the device 200 may be possible. The device 200 is exemplary, and is not intended to limit the disclosure beyond what is explicitly recited in the claims.

The input device 202 enables the user to interact with the device 200, thereby controlling operations of the device 200 through the input device 202. For example, input device 202 may include buttons or switches to control switches, movements, operations, etc. of other components in the device 200. In other embodiments, the input device 202 may include a microphone, a touch screen, a keyboard, a mouse, dynamic input, voice, and the like. In some embodiments, a multimodal system may provide multiple types of input to enable the user to communicate with the device 200.

The output device 204 may be a display device for outputting the oral image sensed (e.g., by the image sensing unit 208) or processed by the device 200. The output device 204 is optional. In some embodiments, the device 200 does not have the output device 204, and the device 200 may transmit the sensed or processed oral image to an external electronic device (e.g., the electronic device 130) through the transceiver 220 to display the sensed or processed oral image through a display device on the electronic device.

Similar to the light emitting diode 122 in FIG. 1, the light emitting diode 206 may generate blue light with a low wavelength to illuminate the teeth in the oral cavity, thereby causing the dental plaque and the dental calculus on the teeth to generate autofluorescence. As discussed above, the light emitting diode 206 may generate the blue light with a wavelength in a range from 370 nm to 430 nm. In some embodiments, the light emitting diode 206 may generate the blue light having a wavelength with 405 nm. The blue light having a wavelength with 405 nm is effective in generating detectable autofluorescence in both normal and abnormal teeth areas (e.g., the dental plaque and the dental calculus). As discussed above, in the present embodiment, the blue light generated by the light emitting diode 206 has a fixed luminous intensity, and the light emitting diode 206 is movable.

Similar to the image sensing unit 124 in FIG. 1, the image sensing unit 208 may be used to sense or capture the oral image, and transmit the oral image to the processor 214, such that the processor 214 may distinguish the dental plaque areas from the dental calculus areas on the teeth in the oral cavity according to the autofluorescence in the sensed oral image. Specifically, after the image sensing unit 208 senses or captures the oral cavity image, the oral cavity image is transmitted to the control circuit 212. Next, the control circuit 212 may perform a program code 218 in the storage device 216 through the processor 214 to analyze and process the oral image, and distinguish the dental plaque areas from the dental calculus areas on the teeth in the oral image. As discussed above, in the present embodiment, the image sensing unit 208 is movable, overlaps the light emitting diode 206 in the top view, and moves simultaneously with the light emitting diode 206. In other embodiments, the image sensing unit 208 does not move.

The storage device 216 is connected to the processor 214. The storage device 216 may be a non-volatile memory and may be a hard disk or another type of computer readable media. The computer readable media may store computer readable data. For examples, the storage device 216 may be magnetic cassettes, flash memory cards, solid state memory devices, digital versatile disks, cartridges, random access memories (RAMs), read only memory (ROM), and hybrids thereof.

The processor 214 may essentially be a completely self-contained computing system, containing multiple cores or processors, a bus, memory controller, cache, etc. A multi-core processor may be symmetric or asymmetric. As discussed above, the processor 214 may be used to analyze and process the oral image to distinguish the dental plaque areas from the dental calculus areas on the teeth in the oral image.

The transceiver 220 is connected to the control circuit 212 to transmit the oral image analyzed and processed by the processor 214 to an electronic device (e.g., the electronic device 130) having a display device (e.g., a computer monitor) through a network (e.g., the network 150), so that the electronic device displays the analyzed and processed oral image. The user may observe the dental plaque and the dental calculus on the teeth in the oral image through the display device of the electronic device.

Figure 3:
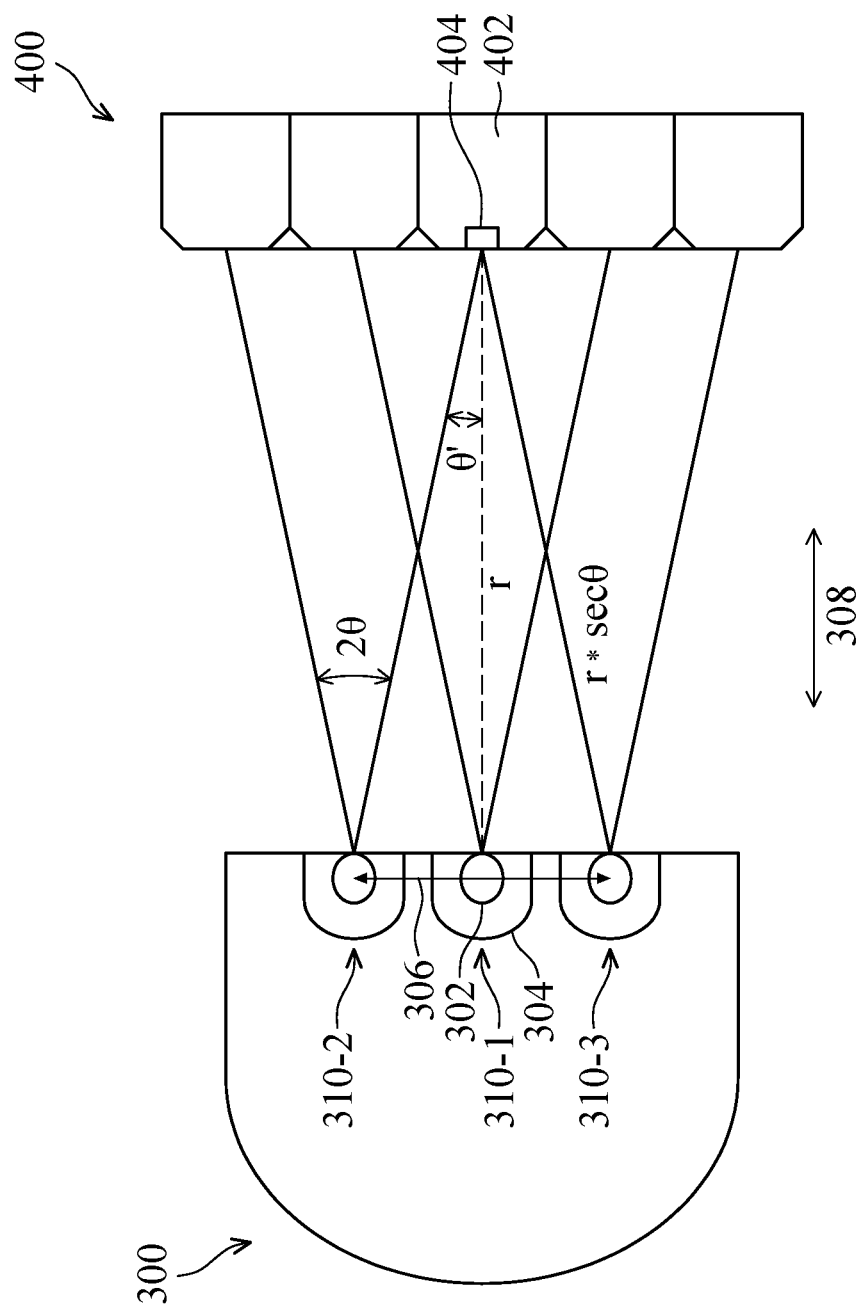
FIG. 3 illustrates a top view of the operation of a device, in accordance with one embodiment of the present disclosure.

FIG. 3 illustrates a top view of the operation of a device 300, in accordance with one embodiment of the present disclosure. The device 300 may be similar or identical to the device 120 of FIG. 1 and the device 200 of FIG. 2. As shown in FIG. 3, the device 300 includes a light source 302 (e.g., a light emitting diode) and an image sensing unit 304. As discussed above, the light source 302 and the image sensing unit 304 are movable in the device 300. In some embodiments, the image sensing unit 304 overlaps the light source 302 in the top view, and the image sensing unit 304 and the light source 302 may move simultaneously. In some embodiments, the light source 302 and the image sensing unit 304 may move in a direction 306. The light source 302 and the image sensing unit 304 are separated by a predetermined distance r from teeth 400 in the oral cavity in a direction 308 perpendicular to the direction 306. In some embodiments, the predetermined distance r is about 0.75 cm, but the present disclosure is not limited thereto. The image sensing unit 304 has a sensing angle 2θ. In some embodiments, the sensing angle 2θ is in a range from about 30° to about 45°, such as 40°. Furthermore, in some embodiments, a blue light generated by the light source 302 has a fixed luminous intensity.

In the present embodiment, the device 300 is used to illuminate an area 404 of a tooth 402 in the teeth 400 as an example to illustrate how to distinguish between the dental plaque and the dental calculus. As shown in FIG. 3, the light source 302 may generate the blue light to illuminate the area 404 on the tooth 402 and may move in the direction 306 in the device 300. As the light source 302 moves to different positions, a distance of the light source 302 from the area 404 changes. For example, when the light source 302 is at a position 310-1, the light source 302 is the predetermined distance r from the area 404, as shown in FIG. 3. When the light source 302 moves to a different location, the light source 302 is separated from the area 404 by a distance r×secθ', where θ' is an angle between the distance of the light source 302 from the area 404 and the direction 308 (normal to the surface of the area 404). In some embodiments, due to the limitation of the sensing angle 2θ of the image sensing unit 304, the maximum distance between the light source 302 and the area 404 is r×secθ.

As discussed above, the blue light generated by the light source 302 has a fixed luminous intensity. As the light source 302 is in different positions, the area 404 may receive different illuminances of the blue light. Specifically, the blue light illuminance (E) received by the area 404 may follow the following formula:

$$E = \frac{(I\cos\theta')}{R^2},$$

where I is the luminous intensity of the blue light generated by the light source 302 (as discussed above, the luminous intensity is fixed), θ' is the angle between the distance of the light source 302 from the area 404 and the direction 308, and R is a distance between the light source 302 and the area 404. According to the formula, it may be known that when I is a fixed value, the illuminance is proportional to cos θ' and inversely proportional to $R^2$. Since the distance between the light source 302 and the area 404 may be expressed as r×secθ', the blue light illuminance (E) received by the area 404 may also follow the following formula:

$$E = \frac{(I\cos^3\theta')}{r^2},$$

where r is the distance between the light source 302 and the area 404 in the direction 308 (i.e., a predetermined distance r). Therefore, according to the formula, it may be known that when I and r are fixed values (the luminous intensity and the predetermined distance are fixed), the illuminance is proportional to $\cos^3\theta'$. More specifically, the greater the angle between the distance of the light source 302 from the area 404 and the direction 308 (i.e., the greater the θ'), the less blue light illuminance received by the area 404.

Figure 4:
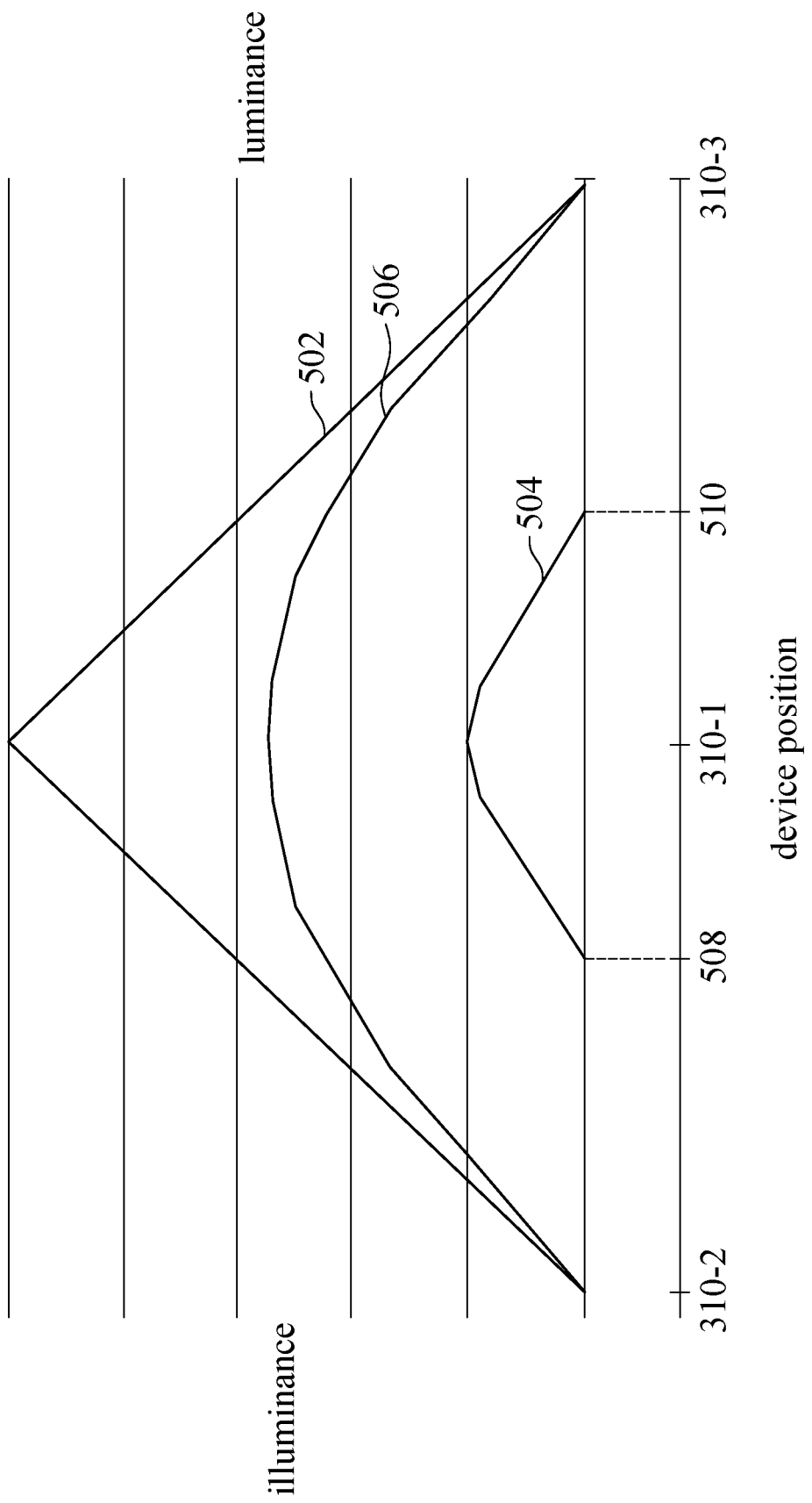
FIG. 4 illustrates a graph of the blue light illuminance received by an area and a graph of the luminance of the autofluorescence of the dental plaque and the dental calculus in the area, in accordance with one embodiment of the present disclosure.

FIG. 4 illustrates a graph of the blue light illuminance received by area 404 and a graph of the luminance of the autofluorescence of the dental plaque and the dental calculus in the area 404, in accordance with one embodiment of the present disclosure. The X-axis represents the position of the device 300, which moves from the position 310-2 to the position 310-1, and then to the position 310-3. The left Y-axis represents the blue light illuminance received by the area 404. The right Y-axis represents the luminance of the autofluorescence of the dental plaque and the dental calculus (if present) in the area 404. It should be understood that the scales of the X-axis and the Y-axis in FIG. 4 are merely relative changes, not absolute values.

As shown in FIG. 4, according to the position of the light source 302, the blue light illuminance received by the area 404 may be distributed as a curve 502. The area 404 may receive maximum blue light illuminance when the light source 302 is at the position 310-1, and the area 404 may receive minimum blue light illuminance when the light source 302 is at the positions 310-2 and 310-3. As such, the dental plaque and the dental calculus in the area 404 generate different luminances of the autofluorescence according to the blue light illuminance received by the area 404.

As shown in FIG. 4, according to the position of the light source 302, the luminance of the autofluorescence of the dental plaque in the area 404 may be distributed as a curve 504, and the luminance of the autofluorescence of the dental calculus in the area 404 may be distributed as a curve 506. Therefore, when the light source 302 is in the different position, the image sensing unit 304 may sense the different luminances of the autofluorescence of the dental plaque and the dental calculus, thereby the processor (e.g., the processor 214) may distinguish the dental plaque areas from the dental calculus areas according to these different luminances of the autofluorescences.

Figure 5:
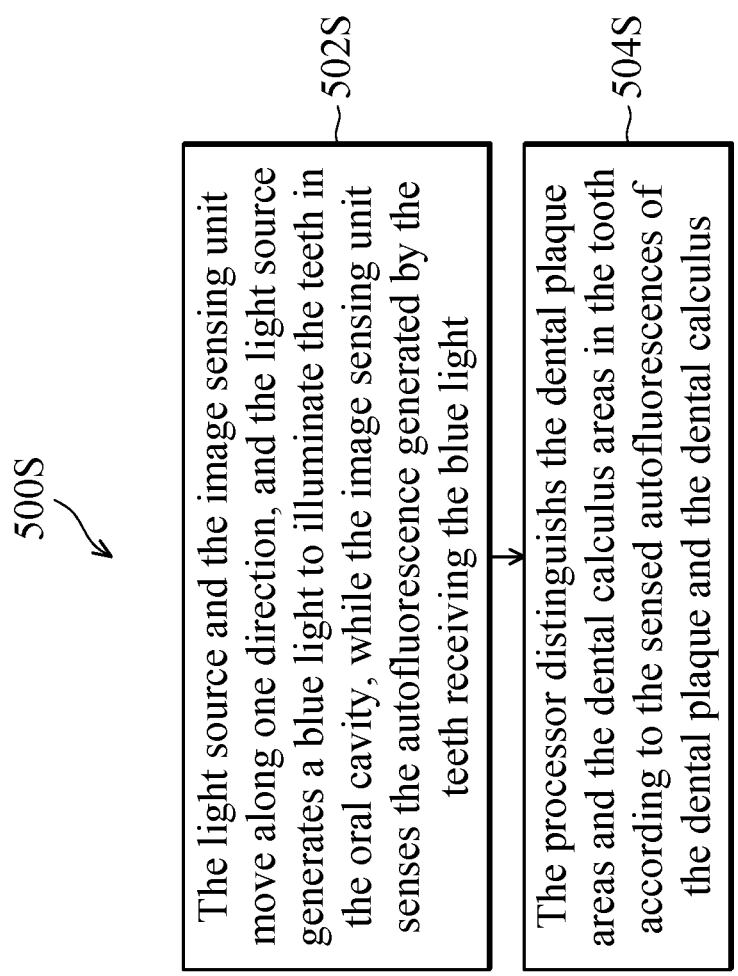
FIG. 5 illustrates a flowchart of an operating method of the device 300, in accordance with one embodiment of the present disclosure.

FIG. 5 illustrates a flowchart of an operating method 500S of the device 300, in accordance with one embodiment of the present disclosure. In operation 502S, the light source 302 and the image sensing unit 304 of the device 300 may move in the direction 306, and the light source 302 generates the blue light to illuminate the teeth in the oral cavity (e.g., the area 404 on the tooth 402), while the image sensing unit 304 senses the autofluorescence generated by the teeth receiving the blue light. For example, as shown in FIG. 3, the light source 302 may move continuously from the position 310-2 to the position 310-3 and generate the blue light to illuminate the area 404 on the teeth 402, while the image sensing unit 304 may also move continuously from the position 310-2 to the position 310-3 and sense the autofluorescence of the dental plaque and the dental calculus in the area 404 on the tooth 402.

In operation 504S, the processor of the device 300 (not shown in FIG. 3) may distinguish the dental plaque areas from the dental calculus areas in the area 404 on the tooth 402 according to the sensed autofluorescences of the dental plaque and the dental calculus.

Figure 6B:
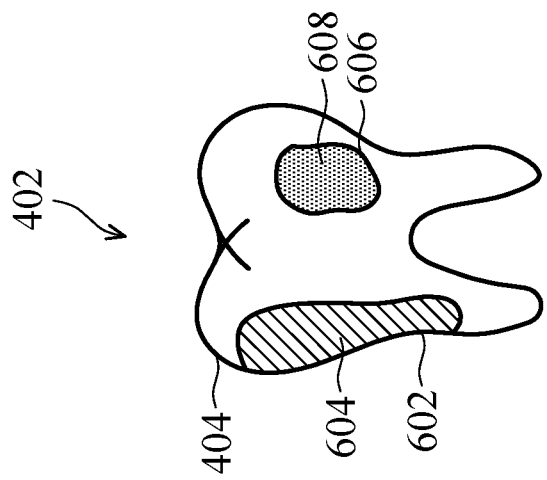
FIG. 6B illustrates a schematic diagram of a tooth with a dental plaque area and a dental calculus area, in accordance with one embodiment of the present disclosure.
Figure 6A:
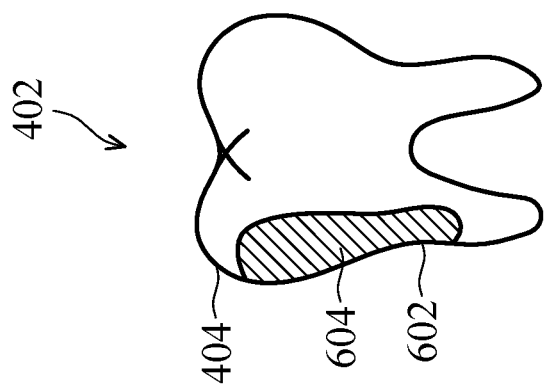
FIG. 6A illustrates a schematic diagram of a tooth with a dental calculus area, in accordance with one embodiment of the present disclosure.

For example, the processor may distinguish the dental plaque areas from the dental calculus areas in the area 404 on the tooth 402 according to the sensing result of the image sensing unit 304 from the position 310-2 to the position 310-3. As shown in FIG. 4, when the light source 302 and the image sensing unit 304 move from the position 310-2 to the position 508, the autofluorescence of the dental calculus may be sensed first, so that the processor may determine the dental calculus areas during the movement of the image sensing unit 304 from the position 310-2 to the position 508. As shown in FIG. 6A, during the movement of the image sensing unit 304 from the position 310-2 to the position 508, the processor may determine that there is a dental calculus area 602 including calculus dental 604 in the area 404 on the tooth 402.

As shown in FIG. 4, when the light source 302 and the image sensing unit 304 move from the position 508 to the position 510, the autofluorescence of the dental plaque begins to be sensed, so that the processor may determine the dental plaque areas during the movement of the image sensing unit 304 from the position 508 to the position 510. As shown in FIG. 6B, during the movement of the image sensing unit 304 from the position 508 to the position 510, the processor may determine that there is a dental plaque area 606 including the dental plaque 608 in the area 404 on the tooth 402.

Finally, as shown in FIG. 4, when the light source 302 and the image sensing unit 304 move from the position 510 to the position 310-3, the blue light illuminance of the light source 302 received in the area 404 is not sufficient to cause the dental plaque 608 in the dental plaque area 606 to generate the autofluorescence, and only the dental calculus 604 in the dental calculus area 602 generates the autofluorescence, so that the processor may thus determine that there is a calculus area 602 including the dental calculus 604 in the area 404 on the tooth 402.

In some embodiments, the processor of the device 300 may distinguish the luminances of the autofluorescences of the dental calculus 604 and the dental plaque 608, thereby distinguishing the dental calculus area 602 from the dental plaque area 606 on the tooth 402. For example, as shown in FIG. 4, it can be seen that the luminance of the autofluorescence of the dental plaque 608 (curve 504) is less than the luminance of the autofluorescence of the dental calculus 604 (curve 506). Therefore, the processor may distinguish the dental calculus area 602 from the dental plaque area 606 on the tooth 402 according to the difference in luminances of the autofluorescences of the dental calculus 604 and the dental plaque 608 sensed by the image sensing unit 304.

The embodiments of the present disclosure offer advantages over existing art, though it should be understood that other embodiments may offer different advantages, not all advantages are necessarily discussed herein, and that no particular advantage is required for all embodiments. By using the embodiments of the present disclosure, the devices and methods of the present disclosure may quickly distinguish the dental plaque from the dental calculus on the teeth to help the user to detect the dental problems quickly.

The foregoing outlines features of several embodiments so that those skilled in the art may better understand the aspects of the present disclosure. Those skilled in the art should appreciate that they may readily use the present disclosure as a basis for designing or modifying other processes and structures for carrying out the same purposes and/or achieving the same advantages of the embodiments introduced herein. Those skilled in the art should also realize that such equivalent constructions do not depart from the spirit and scope of the present disclosure, and that they may make various changes, substitutions, and alterations herein without departing from the spirit and scope of the present disclosure.

What is claimed is:

1. A distinguishing device for dental plaque and dental calculus, comprising:
   a light-emitting diode moving in a first direction in the distinguishing device and adapted to be separated from teeth in an oral cavity by a predetermined distance in a second direction perpendicular to the first direction, wherein the light-emitting diode generates a blue light to illuminate the teeth, so that a dental plaque on the teeth generates a first autofluorescence and a dental calculus on the teeth generates a second autofluorescence;
   an image sensing unit configured to sense the first autofluorescence and the second autofluorescence; and
   a processor coupled to the image sensing unit to distinguish a dental plaque area from a dental calculus area on the teeth according to a difference in luminances of the first autofluorescence and the second autofluorescence.

2. The distinguishing device as claimed in claim 1, wherein the image sensing unit moves in the first direction.

3. The distinguishing device as claimed in claim 2, wherein the image sensing unit overlaps the light-emitting diode in a plan view and moves simultaneously with the light-emitting diode.

4. The distinguishing device as claimed in claim 1, wherein the predetermined distance is about 0.75 cm.

5. The distinguishing device as claimed in claim 1, wherein the blue light generated by the light-emitting diode has a fixed luminous intensity.

6. A method for distinguishing dental plaque and dental calculus, comprising:
   generating a blue light by a light-emitting diode to illuminate teeth in an oral cavity, so that dental plaque on the teeth generates a first autofluorescence and dental calculus on the teeth generates a second autofluorescence, wherein the light-emitting diode moves in a first direction in a distinguishing device and is separated from the teeth by a predetermined distance in a second direction perpendicular to the first direction;
   sensing the first autofluorescence and the second autofluorescence by an image sensing unit; and
   distinguishing a dental plaque area from a dental calculus area on the teeth by a processor according to a difference in luminances of the first autofluorescence and the second autofluorescence.

7. The method as claimed in claim 6, wherein the image sensing unit moves in the first direction to sense the first autofluorescence and the second autofluorescence.

8. The method as claimed in claim 6, wherein the image sensing unit overlaps the light-emitting diode in a plan view and moves simultaneously with the light-emitting diode.

9. The method as claimed in claim 6, wherein the predetermined distance is about 0.75 cm.

10. The method as claimed in claim 6, wherein the blue light generated by the light-emitting diode has a fixed luminous intensity.

11. The distinguishing device as claimed in claim 1, wherein the image sensing unit is moveable in the distinguishing device.

* * * * *